(12) United States Patent
Suckling et al.

(10) Patent No.: US 8,877,174 B2
(45) Date of Patent: Nov. 4, 2014

(54) PHEROMONE COMPOSITION

(75) Inventors: David Maxwell Suckling, Christchurch (NZ); Ashraf M. El-Sayed, Christchuch (NZ)

(73) Assignee: The New Zealand Institute for Plant and Food Research Limited, Sandringham (NZ)

( * ) Notice: Subject to any disclaimer, the term of this patent is extended or adjusted under 35 U.S.C. 154(b) by 0 days.

(21) Appl. No.: 13/997,129

(22) PCT Filed: Dec. 21, 2011

(86) PCT No.: PCT/NZ2011/000269
§ 371 (c)(1),
(2), (4) Date: Sep. 17, 2013

(87) PCT Pub. No.: WO2012/087158
PCT Pub. Date: Jun. 28, 2012

(65) Prior Publication Data
US 2014/0004075 A1    Jan. 2, 2014

Related U.S. Application Data

(60) Provisional application No. 61/425,604, filed on Dec. 21, 2010.

(51) Int. Cl.
*A01N 37/06*    (2006.01)
*A01N 35/02*    (2006.01)

(52) U.S. Cl.
CPC ............... *A01N 37/06* (2013.01); *A01N 35/02* (2013.01)
USPC ........................................... 424/84; 424/405

(58) Field of Classification Search
None
See application file for complete search history.

(56) References Cited

U.S. PATENT DOCUMENTS

2007/0190092 A1*    8/2007   Ino et al. .................... 424/405
2010/0021417 A1*    1/2010   Ogawa et al. ................ 424/84

OTHER PUBLICATIONS

Bellas et al., "Identification of Two Components of the Sex Pheromone of the Moth, *Epiphyas postvittana*(Lepidoptera, Tortricidae)," *Journal of Ecology* 9(4):503-512, 1983.
El-Sayed et al., "Potential of "Lure and Kill" in Long-Term Pest Management and Eradication of Invasive Species," *Journal of Economic Entomology* 102(3):815-835, Jun. 2009.
El-Sayed et al., "Potential of Mass Trapping for Long-Term Pest Management and Eradication of Invasive Species," *Journal of Economic Entomology* 99(5):1550-1564, Oct. 2006.
Foster et al., "Biosynthesis of a monoene and a conjugated diene sex pheromone component of the lightbrown apple moth by Δ11 desaturation," *Experientia* 46: 269-273, 1990.
Gray et al., "Identification and Field Testing of Pheromone Components of *Choristoneura Orae* (Lepidoptera:Tortricidae)," *The Canadian Entomologist* 116: 51-56, Jan. 1984.
Muggleston et al., "Sustained-flight tunnel responses of male lightbrown apple moth to synthetic sex pheromone," *Physiological Entomology* 14:443-449, 1989.
Neal, Jr. et al., "Female Sex Pheromone of *Choristoneura Parallela* (Lepidoptera:Tortricidae)," *Environmental Entomology* 11(4):893-896, 1982.
Rumbo et al., "Spatial Discrimination Between Sources of Pheromone and an Inhibitor by the Light-Brown Apple Moth *Epiphyas postvittana* (Walker) (Lepidoptera:Tortricidae)," *Journal of Chemical Ecology* 19(5):953-962, 1993.
Stephens et al., "Odour quality discrimination for behavioural antagonist compounds in three tortricid species," *Entomologia Experimentalis et Applicata* 127:176-183, 2008.
El-Sayed et al., "New Sex Pheromone Blend for the Lightbrown Apple Moth, *Epiphyas postvittana*," *J. Chem. Ecol.* 37:640-646, 2011.
Suckling et al., "Disruption of Lightbrown Apple Moth *Epiphyas postvittana* (Walker) (Lepidoptera: Tortricidae) Trapping in Nelson, New Zealand," *Aust. J. Zool.* 38:363-373, 1990.

\* cited by examiner

*Primary Examiner* — David J Blanchard
*Assistant Examiner* — Sarah Alawadi
(74) *Attorney, Agent, or Firm* — Seed IP Law Group PLLC

(57) ABSTRACT

The invention relates to a four component pheromone composition that attracts male light brown apple moths and can be used to control moth populations. The pheromone composition comprises (E)-11-tetradecenyl acetate, (E,E)-9,11-tetradecadienyl acetate, (E)-11-tetradecen-1-ol and (E)-11-hexadecenyl acetate.

13 Claims, 7 Drawing Sheets

PHEROMONE COMPOSITION

1. FIELD OF THE INVENTION

The invention relates to a four component pheromone composition that attracts male light brown apple moths (LBAM). The pheromone composition can be used to control moth populations, for example, by disrupting mating.

2. BACKGROUND

The LBAM, *Epiphyas postvittana* (Lepidoptera: Tortricidae) is an important horticultural pest both in its native and introduced habitats in Australia, New Zealand, USA, and the UK. LBAM is best known as a pest insect from tree fruits, including apples, pears, citrus, peaches, nectarines, apricots, vines, berryfruit, and to a lesser extent from forestry, vegetable, and flower crops. LBAM larvae feed on leaves and the surface of fruit typically by webbing a leaf to a fruit to create a protected shelter. This causes unsightly blemishes on fruit and can lead to secondary disease, such as causing rots in crops such as grapes.

For most lepidopterous species, reproductive behavior consists of the female releasing a volatile sex pheromone that elicits upwind flight in males of the same species. The males orient to the source to effect copulation. Since most lepidopterous species use many of the same pheromone compounds for sexual communication, multi-component blends can be critical for species specificity (El-Sayed, 2010).

Sex pheromones can be used to control lepidopterous populations in a variety of ways including attracting the insects to traps or poisons and disrupting their mating.

The sex pheromone of the LBAM was initially identified as a two-component blend of (E)-11-tetradecenyl acetate (E11-14Ac) and (E,E)-9,11-tetradecadienyl acetate (E9E11-14Ac), (Bellas et al., 1983).

It was found that the peak male catch occurred when a 100:5 ratio of E11-14Ac and E9E11-14Ac respectively was used.

Further work on the sex pheromone of this insect provided no evidence for the involvement of additional compounds in the mating signal, although Foster and Roelofs (1990) found the saturated 14Ac compound to be present in glands at about 10%. However, Muggleston and Foster (1989) found no evidence of a behavioral role for this compound in wind tunnel assays.

The habitat of the LBAM continues to expand, with insects now confirmed in California and Europe. It is therefore an object of the invention to provide an improved pheromone composition, or to at least provide the public with a useful choice.

The invention relates generally to a pheromone composition comprising four components: (E)-11-tetradecenyl acetate (E11-14Ac), (E,E)-9,11-tetradecadienyl acetate (E9E11-14Ac), (E)-11-tetradecen-1-ol (E11-14OH) and (E)-11-hexadecenyl acetate (E11-16Ac).

3. SUMMARY OF THE INVENTION

In one aspect the invention provides a pheromone composition comprising
(a) E11-14Ac
(b) E9E11-14Ac
(c) E11-14OH and
(d) E11-16Ac
wherein (a) and (b) are present in a weight ratio of about 50:5 to about 150:5, preferably about 80:5 to about 120:5, more preferably about 100:5, and (c) and (d) are present in amounts that increase the effectiveness of the composition at attracting male LBAM relative to a pheromone composition comprising (a) and (b) only.

In one embodiment (c) and (d) are present in a ratio of about 5:1 to about 1:2, preferably a ratio of about 3:1 to 1:1, more preferably a ratio of about 2:1.

In one embodiment (a) and (c) are present in a ratio of about 300:1 to about 20:1, preferably a ratio of about 200:1 to about 50:1, more preferably a ratio of about 100:1.

In one aspect the invention provides a pheromone composition comprising
   (a) E11-14Ac
   (b) E9E11-14Ac
   (c) E11-14OH and
   (d) E11-16Ac
wherein (a), (b), (c), and (d) are present in the following weight ratios:
   (a) about 50 to about 150, preferably 80 to 120, more preferably 100;
   (b) about 2 to about 10, preferably 3 to 8, more preferably 5;
   (c) about 1;
   (d) about 0.1 to about 2, preferably about 0.3 to about 1, more preferably 0.5.

In another aspect the invention provides a pheromone composition comprising
   (a) E11-14Ac
   (b) E9E11-14Ac
   (c) E11-14OH and
   (d) E11-16Ac
wherein (a), (b), (c), and (d) are present in the following weight ratios:
   (a) about 100;
   (b) about 2 to about 10, preferably 3 to 8, more preferably 5;
   (c) about 0.2 to about 5, preferably about 0.5 to about 2, more preferably about 1;
   (d) about 0.1 to about 2, preferably about 0.3 to about 1, more preferably 0.5.

In another aspect the invention provides a pheromone composition comprising
   (e) E11-14Ac
   (f) E9E11-14Ac
   (g) E11-14OH and
   (h) E11-16Ac
wherein (a), (b), (c), and (d) are present in the following weight ratios:
   (e) about 100;
   (f) about 100;
   (g) about 1 to about 50;
   (h) about 1 to about 50.

In another aspect the invention provides a pheromone composition comprising
   (a) E11-14Ac
   (b) E9E11-14Ac
   (c) E11-14OH and
   (d) E11-16Ac
wherein (a), (b), (c), and (d) are present in the following weight ratios:
   (a) about 50 to about 150, preferably 80 to 120, more preferably 100;
   (b) about 5;
   (c) about 0.2 to about 1, preferably about 0.5 to about 2, more preferably about 1;
   (d) about 0.1 to about 2, preferably about 0.3 to about 1, more preferably 0.5.

In another aspect the invention provides a pheromone composition comprising
(a) E11-14Ac
(b) E9E11-14Ac
(c) E11-14OH and
(d) E11-16Ac
wherein (a), (b), (c), and (d) are present in the following weight ratios:
(a) about 50 to about 150; preferably 80 to 120, more preferably 100;
(b) about 2 to about 10, preferably 3 to 8, more preferably 5;
(c) about 0.2 to about 5, preferably about 0.5 to about 2, more preferably about 1;
(d) about 0.5.

In another aspect the invention provides a pheromone composition comprising
(a) E11-14Ac
(b) E9E11-14Ac
(c) E11-14OH and
(d) E11-16Ac
wherein (a), (b), (c), and (d) are present in the following weight ratios:
(a) about 100;
(b) about 5;
(c) about 1;
(d) about 0.5.

In one embodiment the pheromone composition is included in an inert solid or liquid carrier. Preferably the carrier is a volatile organic solvent. Preferably the volatile organic solvent is selected from the group comprising pentane, hexane, heptanes, ethanol, methylene chloride or mixtures thereof.

In one aspect the invention provides a pheromone composition comprising
(a) E11-14Ac
(b) E9E11-14Ac
(c) E11-14OH and
(d) E11-16Ac
and a liquid carrier
wherein the concentration of (a) is about 250 to about 750 µg/ml, preferably about 400 to about 600 µg/ml, more preferably about 500 µg/ml;
the concentration of (b) is about 10 to about 40 µg/ml, preferably about 20 to about 30 µg/ml, more preferably about 25 µg/ml;
the concentration of (c) is about 2 to about 8 µg/ml, preferably 4 to about 6 µg/ml, more preferably 5 µg/ml and
the concentration of (d) is about 1 to about 4 µg/ml, preferably about 2 to about 3 µg/ml, more preferably about 2.5 µg/ml.

In one embodiment the concentration of (a) is about 500 µg/ml, (b) is about 25 µg/ml, (c) is about 5 µg/ml and (d) is about 2.5 µg/ml.

In one embodiment the liquid carrier is an organic solvent comprising pentane, hexane, heptanes, ethanol, methylene chloride or mixtures thereof.

In one aspect the invention provides a pheromone composition consisting of
(a) E11-14Ac
(b) E9E11-14Ac
(c) E11-14OH and
(d) E11-16Ac
wherein (a) and (b) are present in a weight ratio of about 50:5 to about 150:5, preferably about 80:5 to about 120:5, more preferably about 100:5, and (c) and (d) are present in amounts that increase the effectiveness of the composition at attracting male LBAM relative to a pheromone composition comprising (a) and (b) only.

In one aspect the invention provides a method of attracting male LBAM to a location comprising providing an effective amount of a pheromone composition of the invention to the location.

In one embodiment the male LBMA are subsequently or simultaneously exposed to a killing agent that kills the moths.

In one embodiment the location comprises one or more traps. Preferably, the traps include a killing agent. In one embodiment the killing agent is an insecticide.

In one aspect the invention provides a method of disrupting mating of the LBAM comprising providing to a population of LBAM an effective amount of the pheromone composition of the invention.

In the above aspects of the invention:
In one embodiment, the pheromone composition of the invention is substantially free of Z11-14:Ac.

In one embodiment the pheromone composition is included in a carrier and/or dispenser. In one embodiment the carrier is selected from an organic solvent comprising pentane, hexane, heptanes, ethanol, methylene chloride or mixtures thereof. In another embodiment the carrier is a matrix of waxes and oils from which the pheromone can be released.

In one embodiment the dispenser is a rubber septa or a polyethylene dispenser.

In one embodiment the trap is a sticky trap such as a delta trap.

In one embodiment the pheromone composition of the invention is provided in a rubber septa, which is associated with a sticky trap. Preferably, the sticky trap includes an insecticide.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

4. BRIEF DESCRIPTION OF FIGURES

FIG. 1 shows the coupled GC-EAD responses of antenna of male LBAM to female gland extract. Chromatographic column and conditions: A non-polar VF5-MS capillary column, 30 m by 0.25 mm i.d.; Temperature program 80° C./1 min, 10° C./min to 240° C., 240° C./30 min.

FIG. 2 shows the mean catch±SE of male LBAM caught in traps baited with a three component blend containing a constant proportion of E11-14Ac and E9E11-14Ac (0.1:0.005 mg) plus varying amounts of E11-14OH (0, 0.001, 0.002, and 0.005 mg, from left to right). The experiment was conducted from 18 Feb. 2010 to Apr. 3, 2010 in apple orchards and a total of 911 male moths were captured. Treatments labeled with the same letters are not significantly different ($P>0.05$).

FIG. 3 shows the mean catch±SE of male LBAM caught in traps baited with a three component blend containing a constant proportion of E11-14Ac and E9E11-14Ac (0.1:0.005 mg) plus varying amounts of E11-16Ac; Top (0, 0.001, 0.002, and 0.005 mg, from left to right); Bottom (0, 0.0001, 0.0005, and 0.001 mg, from left to right). The experiment was conducted from Nov. 3, 2010 to Dec. 4, 2010 in apple orchards and a total of 556 male moths were captured. Treatments labeled with the same letters are not significantly different ($P>0.05$).

FIG. 4 shows the mean catch±SE of male LBAM caught in traps baited, from left to right, with four different pheromone blends female LBAM was used as positive control and blank as negative control. The experiment was conducted from 30 Apr. 2010 to 15 May 2010 in apple orchards and a total of 744 male moths were captured. Treatments labeled with the same letters are not significantly different (P>0.05). The four different pheromone blends, from left to right, were a nine component blend with all compounds identified in the gland; four component blend with all compounds that elicited the EAD response; and the known binary blend (E11-14Ac and E9E11-14Ac).

FIG. 5 shows the mean catch±SE of male LBAM caught in traps baited with four different pheromone blends; a seven component blend containing all compounds identified in the gland without the saturated aldehyde; a six component blend containing all compounds identified in the gland without the saturated acetate; a four component blend containing all compounds that elicited the EAD response; and the known binary blend (E11-14Ac and E9E11-14Ac) and at far right, blank as negative control. The experiment was conducted from Nov. 5, 2010 to 25 May 2010 in apple orchards and a total of 659 male moths were captured. Treatments labeled with the same letters are not significantly different (P>0.05).

5. DETAILED DESCRIPTION OF THE INVENTION

5.1 Definitions

Figure 1:
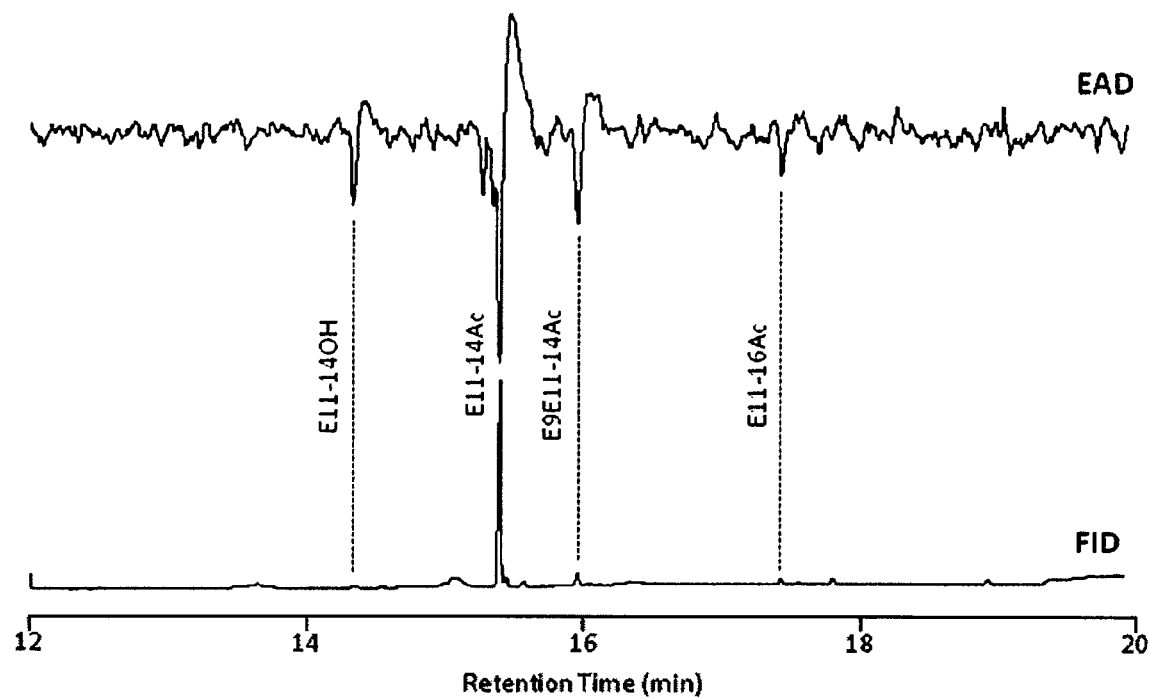

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

5.2 Pheromone Compositions of the Invention

The pheromone compositions of the invention contain a four component blend of compounds including two compounds previously identified as LBAM attractants and two newly identified additional compounds.

An investigation into the chemical composition of the sex pheromone gland of the LBAM identified seven candidate compounds, in addition to the two known LBAM pheromones (E11-14Ac and E9E11-14Ac). The candidate compounds were (E)-1'-tetradecen-1-ol (E11-14OH), tetradecyl acetate (14Ac), hexadecanal (16Ald), (E)-11-hexadecenyl acetate (E11-16Ac), hexadecyl acetate (16Ac), octadecanal (18Ald), and octadecyl acetate (18Ac).

As discussed in Example 1, only four of the nine compounds elicited any electrophysiological response (E11-14OH, E11-14Ac, E9E11-14Ac, and E11-16Ac).

The two compounds E11-14OH and E11-16Ac are both known but have not been previously identified as being present in the sex pheromone gland of LBAM females.

E11-14OH has been reported as pheromone compound in many leafrollers, for example the Spruce budworm, *Choristoneura orae* (Gray et al., 1984); and the spotted fireworm, *Choristoneura parallela* (Neal et al., 1982). In contrast, E11-16Ac has not been reported as a sex pheromone in any other tortricid species, but is abundant amongst Crambidae, Noctuidae and Satumiidae (El-Sayed 2010).

It was determined that the two active newly identified compounds (E11-14OH and E11-16Ac) greatly increased the efficacy of the known two component blend of E11-14Ac and E9E11-14Ac as a LBAM attractant. For example, when present in a ratio of 100 parts E11-14Ac:5 parts E9E11-14Ac:1 part E11-14OH and 0.5 parts E11-16Ac, the mean number of male LBAM captured is almost doubled compared to use of the conventional mixture of 100 parts E11-14Ac:5 parts E9E11-14Ac. While smaller relative amounts of the minor components (E11-14OH and E11-16Ac) are generally preferred, the invention encompasses compositions where the minor components make up to a third of the composition. For example, where E11-14Ac and E9E11-14Ac are present in a 1:1 ratio and the minor components, in a ratio of 0.5:0.5.

The increase in efficacy of the four component pheromone compositions of the invention means they may be used in situations where the standard two component blend cannot. For example, in areas of low population density such as newly invaded habitats or where environmental conditions are such that the two-component blend would not be sufficiently attractive.

The enhanced efficacy of the pheromone composition of the invention also means that a smaller amount can be used to attract the LBAM, resulting in cost savings.

Accordingly, the invention provides a pheromone composition comprising
 (a) E11-14Ac
 (b) E9E11-14Ac
 (c) E11-14OH and
 (d) E11-16Ac
wherein (a) and (b) are present in a weight ratio of about 50:5 to about 150:5, preferably about 80:5 to about 120:5, more preferably about 100:5, and (c) and (d) are present in synergistic amounts that increase the effectiveness of the composition at attracting LBAM relative to a pheromone composition comprising (a) and (b) only.

The pheromone compositions of the invention may be provided alone or may be included in a carrier and/or a dispenser. The carrier may be an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include but are not limited to water; alcohols, particularly ethanol, butanol or glycol, as well as their ethers or esters, particularly methylglycol acetate; ketones, particularly acetone, cyclohexanone, methylethyl ketone, methylisobutylketone, or isophorone; alkanes such as hexane, pentane, heptanes; aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

The pheromone compositions of the invention may be formulated so as to provide slow release into the atmosphere, and/or so as to be protected from degradation following release. For example, the pheromone compositions may be included in carriers such as microcapsules, biodegradable flakes and paraffin wax-based matrices.

The pheromone composition of the invention may be provided in combination with other pheromones or attractants provided that the other compounds do not substantially interfere with the activity of the composition.

The pheromone compositions of the invention may also include insecticides. Examples of insecticides that may be used in combination with the pheromone composition of the invention include, but are not limited to buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, fenpropathrin, kinoprene, insecticidal soap or oil and mixtures thereof.

In some instances the pheromone composition is provided by direct release from the carrier. For example Min-U-Gel® (a highly absorptive Attapulgite clay) can be impregnated with a pheromone composition of the invention. In another example, the pheromone composition may be mixed in a carrier paste that can be applied to trees and other plants. Insecticides added to the paste will kill LBAM that contact the paste. Baits or feeding stimulants can also be added to the carrier.

In other applications the pheromone composition is included in a dispenser, either directly on in association with a carrier. A dispenser allows for release of the pheromone composition. Any suitable dispenser known in the art can be used.

Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa.

An example of a dispenser is a sealed polyethylene tube containing the pheromone composition of the invention where a wire is fused inside the plastic so the dispenser can be attached by the wire to a tree or shrub.

It is to be understood that a skilled worker will be able, without undue experimentation, with regard to that skill and this disclosure, to select suitable carriers and/or dispensers for the desired mode of application, storage, transport or handling (El-Sayed et al., 2006; El-Sayed et al., 2009).

5.3 Methods of the Invention

The methods of the invention use the pheromone compositions of the invention to attract male LBAM. The pheromone compositions of the invention can be used to attract male LBAM as part of a strategy for insect monitoring, mass trapping, lure and kill or mating disruption (El-Sayed et al., 2006; El-Sayed et al., 2009).

In the methods of the invention the pheromone composition may be provided alone or in conjunction with a carrier and/or dispenser. The dispenser may also comprise or include a trap. A killing agent may be incorporated into the trap, such as a sticky or insecticide-treated surface, a restricted exit, insecticide vapour or an electric grid.

In a preferred embodiment, the killing agent is an insecticide.

LBAM populations can be surveyed or monitored by counting the number of insects caught in the traps. Inspection by a horticulturist may provide information about the life stage of a population. Knowing where insects are, how many of them there are, and their life stage enables informed decisions to be made as to where and when insecticides or other treatments are warranted. For example, a discovery of a high LBAM population may necessitate the use of methods for removal of the insect. Early warning of an infestation in a new habitat may allow action to be taken before the population becomes unmanageable. Conversely, a discovery of a low LBAM population may lead to a decision that it is sufficient to continue monitoring the population. LBAM populations may be monitored regularly so that the insects are only controlled when they reach a certain threshold. This provides cost-effective control of the insects and reduces the environmental impact of the use of insecticides.

Mass trapping involves placing a high density of traps in a crop to be protected so that a high proportion of the insects are removed before the crop is damaged.

Lure and kill techniques are similar except once the insect is attracted to a lure, it is subjected to a killing agent.

Where the killing agent is an insecticide, the dispenser may also contain a bait or feeding stimulant that will entice the LBAM to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Sticky traps are available from Olson Products, Medina, Ohio, USA and come in a range of different colours.

Water traps include pans of water and detergent that are used to trap insects. The detergent destroys the surface tension of the water, causing insects that are attracted to the pan, to drown in the water. One way traps allow an insect to enter the trap but prevent it from exiting.

The traps of the invention may be coloured brightly, to provide additional attraction for the LBAM.

The trap is positioned in an area infested (or potentially infested) with LBAM. Generally, the trap is placed on or close to a tree or large plant. The aroma of the pheromone attracts the male LBAM to the trap. The insects may then be caught, immobilised and/or killed within the trap, for example, by the killing agent present in the trap.

The pheromone compositions of the invention can also be used to attract LBAM away from vulnerable crop areas.

The sex pheromone compositions of the invention can also be used to disrupt mating. Strategies of mating disruption include confusion, trail-masking and false-trail following. Constant exposure of LBAM to a high concentration of pheromone composition can prevent the male from responding to normal levels of the pheromone released by females. Trail-masking uses the pheromone composition to destroy the trail of pheromones released by females. False-trail following is carried out by laying numerous spots of pheromone composition in high concentration to present the male with many false trails to follow. When released in sufficiently high quantities, the male LBAM are unable to find the natural source of the sex pheromones (the female LBAMs) so that mating cannot occur.

As will be apparent to one of skill in the art, the amount of pheromone composition required for a particular application may vary depending on several factors such as (1) the type and level of infestation, (2) the type of composition used, (3) the concentrate of the active components, (4) how the composition is provided, for example, the type of dispenser used; (5) the type of location to be treated, (6) the length of time the method is to be used for, and (7) environmental factors such as temperature, wind speed and direction, rainfall and humidity. It should be understood that a person of ordinary skill in the art will be able, without undue experimentation, having regard to that skill and this disclosure, to determine an effective amount of a composition of this invention for a given application.

An effective amount for attracting male LBAM is the minimum amount of composition needed to attract male LBAM to a location when compared to the same untreated location. This can be measured by comparing the numbers of insects attracted to the baited location with the number of insects attracted to the location when unbaited. The precise amount needed to be effective will vary with the particular formulation of the composition.

Disruption of mating may necessitate release of the pheromone composition by aerial application. An amount effective to disrupt mating can be determined by comparing the number of male LBAM caught in traps baited with virgin female LBAM (or lures that approximate virgin females in the absence of the composition of the invention) with the number of male LBAM caught in traps at a location to which the pheromone composition of the invention has been provided. If the pheromone composition is effective, fewer male moths will be caught in the traps.

Typically, the amount of pheromone composition provided is such that about 0.5 mg to about 5 mg of the four active components combined is supplied. For example, in a typical method of the invention the pheromone composition of the invention is provided in the form of 100 µg E11-14Ac, 5 µg E9E11-14Ac, 1 µg E11-14OH, and 0.5 µg E11-16Ac applied to a rubber septa.

The following non-limiting examples are provided to illustrate the present invention and in no way limits the scope thereof.

6. EXAMPLES

6.1 2010 Experiments

Materials and Methods

Insects.

A colony of LBAM was established and maintained at Mt. Albert Research Center (Auckland). The insects were sexed in the pupal stage, and adult males were allowed to emerge in isolation from the females. Males and females were kept at 22±2° C., 18L:6D, they were provided with water and were 2-3 days old at the time of testing.

Chemicals

All compounds used as authentic standards in the chromatographic analysis or in the field trapping experiments were >97% pure by GC analysis and stored at −80° C. until used. Samples of (E)-11-tetradecenyl acetate (E11-14Ac), (E,E)-9,11-tetradecadienyl acetate (E9E11-14Ac), (E)-11-tetradecen-1-ol (E11-14OH), Hexadecanal (16Ald); (E)-11-hexadecenyl acetate (E11-16Ac), Hexadecyl acetate (16Ac), Octadecyl acetate (18Ac) were purchased from Plant Research International, Wageningen, The Netherlands. The Tetradecyl acetate (14Ac) was purchased from Bedoukian Research Inc., Connecticut, USA and the Octadecanal (18Ald) was synthesized at Plant and Food Research. All blends of synthetic compounds were applied to the large "well" of red rubber septa (West Pharmaceutical Services, Kearney, N.E., USA) in 200 µl of n-hexane GR (Merck Ltd, New Zealand). The solvent was allowed to evaporate in a fume hood and the septa were stored in heat-sealed foil bags at −20° C. until ready for use.

Pheromone Gland Extraction

The sex pheromone glands of 2-3 day old calling females (>10 female) were removed during the first two hours of the scotophase and extracted in ca. 20 µl of hexane for 5-10 min. Chemical analysis of the gland extracts was performed using GC-EAD or GC-MS as described below. Quantification of the amount of each compound in the female sex pheromone gland was conducted using external standard method.

Gas Chromatography-Mass Spectrometry (GC-MS) Analysis.

The gland extracts and synthetic chemicals were analyzed on a Saturn 2200 GC-MS (Varian Walnut Creek, Calif., USA) using an ionization voltage of 70 eV and a mass range of 30 to 650, equipped with two different capillary columns; a non polar 30 m×0.25 mm i.d.×0.5 µm, VF5-MS capillary column (Factor four, Varian Inc, USA) and a polar 30 m×0.25 mm i.d.×0.5 µm, VF23-MS capillary column (Factor Four, Varian Inc, USA) and splitless injection. In both columns, the oven was programmed from 80° C. (held for 1 min) to 240° C. at 10° C./min, held for 13 minutes. Compounds were identified by comparing retention times and mass spectra with those of synthetic compounds.

Gas Chromatography-Electroantennogram Detector (GC-EAD)

Coupled GC-EAD analysis of pheromone gland extracts was conducted on a Varian 3800 GC equipped with a flame ionization detector (FID) and a splitless injector. The column effluent was split 1:1 between the FID and EAD apparatus. Antennal depolarization was detected using a high-resistance EAD Probe, Signal Interface Box, Type ID-02 and Intelligent Data Acquisition Controller, Type IDAC-02 (Syntech, Hilversum, The Netherlands). Antennae from 2-3 d old males were excised at the base and attached to the silver electrodes housed in a saline glass electrode using a micromanipulator. Up to 10 antennal preparations were used for GC-EAD analyses. A non polar 30 m×0.25 mm i.d.×0.5 µm, VF5-MS capillary column (Factor four, Varian Inc, USA) and a Graph pack—3D/2 crosspiece splitter (Gerstel GmbH & Co, KG, Germany) were used for the analyses. The oven temperature was programmed from 80° C. (held for 1 min) to 220° C. at 10° C./min, held for 13 minutes. Helium was used as the carrier gas.

Field Trapping Experiments.

Red delta traps made of plastic corflute with an adhesive-coated base (Suckling and Shaw, 1992) were baited with each pheromone blend and placed in 5 rows, with five replicates of each treatment in a randomized block design. Traps were positioned 1.7 m above the ground in each trap tree, and were spaced 20 m apart in each row. Each treatment was assigned randomly to a trap tree within each row of trees. Septa were placed in the center of the sticky base. Sticky bases were removed weekly during the experimental period for later counting. A trap with a blank lure was used as control.

Data Analysis

The effect of treatment on the mean number of LBAM captured was tested using ANOVA (SAS Institute Inc., 1998) after variances were stabilized using the $\sqrt{x}$ transformation. Significantly different treatment means were identified using Fisher's Protected Least Significant Difference Test (SAS Institute Inc., 1998).

Example 1

Chemical and GC-EAD Analyses of the Pheromone Gland Extracts of Female LBAM

Chemical analyses of the pheromone gland extracts of female LBAM found E11-14Ac and E9E11-14Ac, in addition to seven additional minor compounds that have a lepidopterous type pheromone structure (Table 1).

The first compound had the diagnostic ions m/z of 55, 67, 81, 95, 109, 123 and eluted earlier than the main pheromone compound on a non polar column, suggesting that it was either saturated aldehyde or monounsaturated alcohol or acetate. The lack of an m/z 61 ion excluded the acetate functionality, suggesting that it would be either saturated aldehyde or monounsaturated alcohol. The retention time and kovats retention indices of this compound matched E11-14OH on both polar and non-polar columns. Four of the new compounds has diagnostic molecular ion m/z 61, which is characteristic of acetate compounds. Three of these compounds had diagnostic ions m/z of 69, 83, 97, 111, and 125, suggesting saturated acetate compounds. Both the retention time and kovats retention indices of these three compounds matched 14Ac, 16Ac and 18Ac, on both polar and non-polar columns. The fourth acetate structure had diagnostic ions m/z of 67, 81, 95, 109, 123, and 222 suggesting monounsaturated 16 carbons acetate compound. Both the retention time and kovats retention indices of this compound matched E11-16Ac on both polar and non-polar columns. The final two structures had the diagnostic ions m/z of 55, 67, 81, 95, 109, 123 suggesting either saturated aldehyde or monounsaturated alcohol. The retention time and kovats retention indices of these two compounds matched 16Ald and 18Ald on both polar and non-polar columns.

TABLE 1

Ratio and retention indices of the nine candidate pheromone compounds in the sex pheromone gland extracts of female LBAM

| Compound | ng/female[a] | Ratio (%) | Non Polar VF5-MS | Polar VF23-MS |
|---|---|---|---|---|
| E11-14 OH | 0.01 | 0.1 | 1679 | 2310 |
| E11-14 Ac | 9.18 | 100 | 1804 | 2254 |
| 14 Ac | 0.52 | 5.7 | 1809 | 2204 |
| 16 Ald | 0.58 | 6.3 | 1824 | 2320 |
| E9,E11-14 Ac | 0.48 | 7.1 | 1868 | 2480 |
| E11-16 Ac | 0.05 | 0.7 | 1999 | 2466 |
| 16 Ac | 0.42 | 4.6 | 2010 | 2422 |
| 18 Ald | 0.76 | 8.3 | 2028 | 2552 |
| 18Ac | 0.04 | 0.4 | 2108 | 2641 |

[a] n = 5

Analysis of the pheromone gland extracts by GC-EAD revealed that four compounds consistently elicited a response from male moth antennae. E11-14Ac elicited the strongest EAD response followed by both E9E11-14Ac, E11-14OH, while E11-14Ac elicited the weakest EAD response (see FIG. 1).

Example 2

Optimization of the Ratio of E11-14OH and E11-16Ac

The previously identified two-component blend containing a constant proportion of E11-14Ac and E9E11-14Ac (0.1:0.005 mg) was supplemented by varying amounts of the other two EAD active compounds E11-14OH or E11-16Ac, i.e., 0, 0.001, 0.002, and 0.005 mg and tested in field trapping experiments as described above. An additional experiment was required to test lower concentrations of E11-16Ac. In this experiment, the two component blend containing a constant proportion of E11-14Ac and E9E11-14Ac (0.1:0.005 mg) was supplement with varying amounts of E11-16Ac, i.e., 0, 0.0001, 0.0005, and 0.001 mg and field tested.

Figure 2:
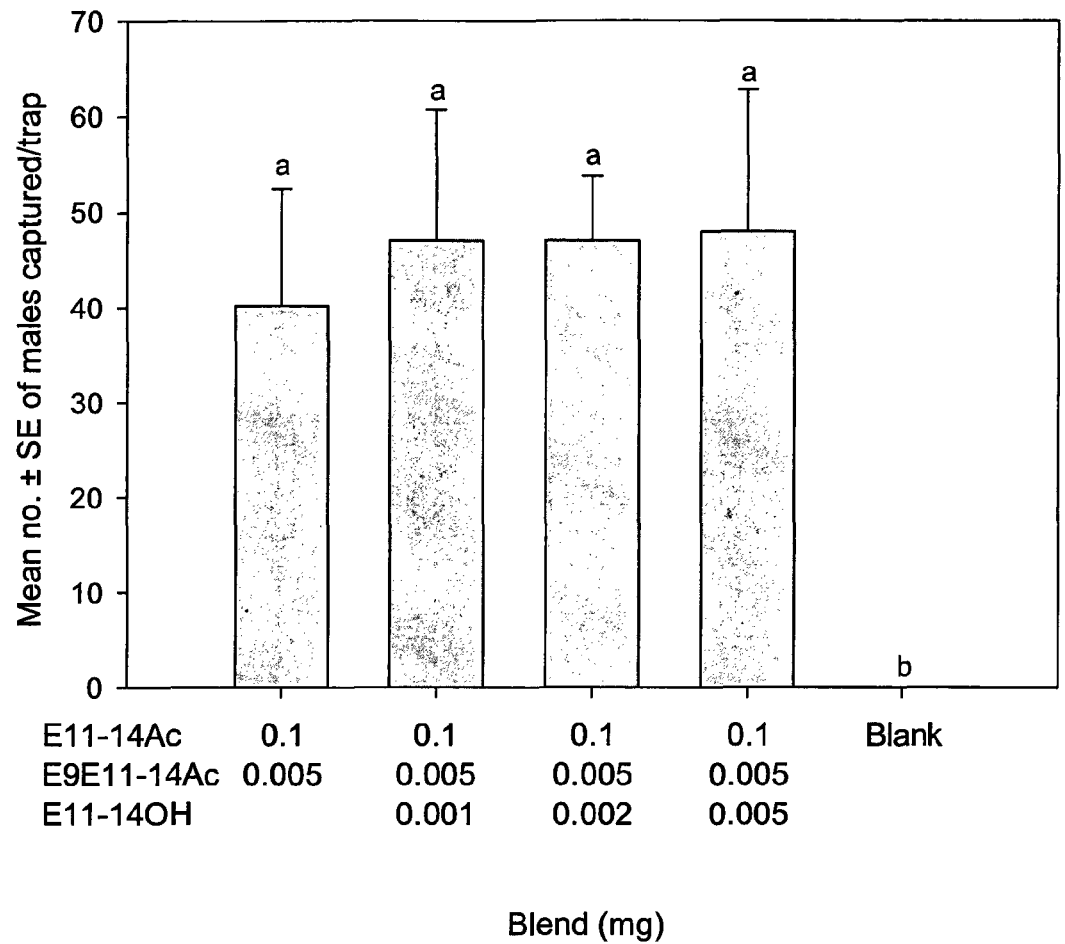
Figure 3:
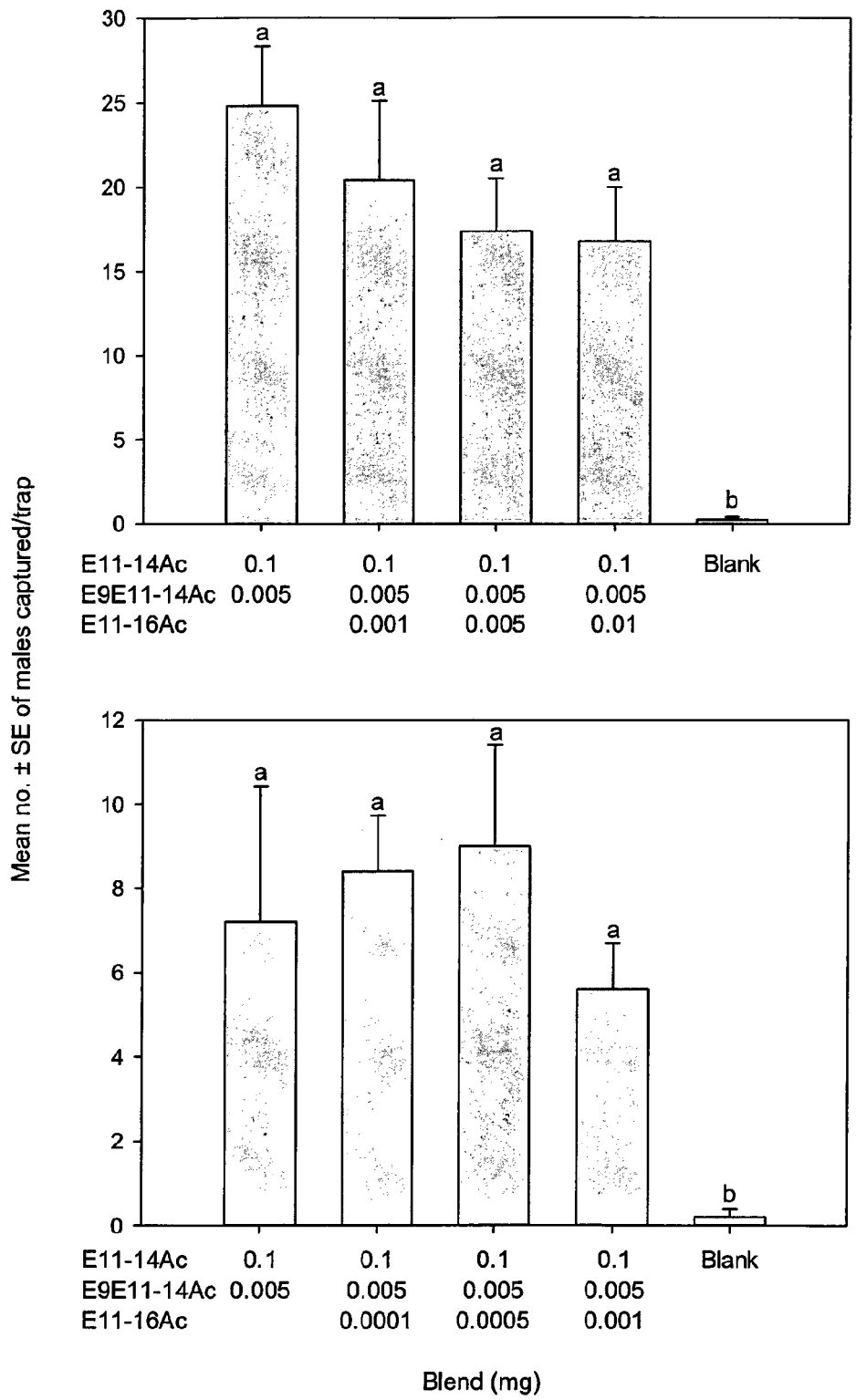

The addition of 1, 2 or 5% of E11-14OH to the two-component blend of E11-14Ac and E9E11-14Ac did not result in any significance increase in the number of LBAM males caught in the traps (see FIG. 2). Similarly, the addition of 1 or 2 or 5% of E11-16Ac to the two-component blend did not result in a significance increase in the number of LBAM males caught (see FIG. 3 top). In fact, the number of males caught declined as the concentration of E11-16Ac increased (see FIG. 3 top). This led to another experiment designed to test lower concentrations of E11-16Ac (i.e. 0.1 or 0.5 or 1%) in conjunction with the two component blend of E11-14Ac and E9E11-14Ac. In this experiment, no peak in male catch was observed at any of the ratios tested (FIG. 3 bottom).

Example 3

Testing Various Blends of Compounds

The relative attractiveness of various pheromone blends was field tested using the method described above:
  a nine-component blend (E11-14OH, E11-14Ac, 14Ac, E9E11-14Ac, E11-16Ac, 16Ald, 16Ac, 18Ald, and 18Ac in ratio of 0.001, 0.1, 0.005, 0.005, 0.0005, 0.005, 0.005, 0.01, and 0.005 mg respectively),
  a four-component blend (E11-14OH, E11-14Ac, E9E11-14Ac, E11-16Ac, in ratio of 0.001, 0.1, 0.005, and 0.0005 mg respectively), and
  a two-component blend (E11-14Ac, E9E11-14Ac, in ratio of 0.1 and 0.005 mg respectively).

Trap baited with a single caged female was used as positive control, and trap baited with a blank lure was used as negative control.

The quality of the pheromone blend significantly affected the number of male caught in the trap ($F_{5,78}=9.8$, $p=0.0001$). The four-component blend caught the highest number of males and was significantly higher than the two-component blend (see FIG. 4). No significant different was observed between the nine-component blend and the two-component blend.

Figure 4:
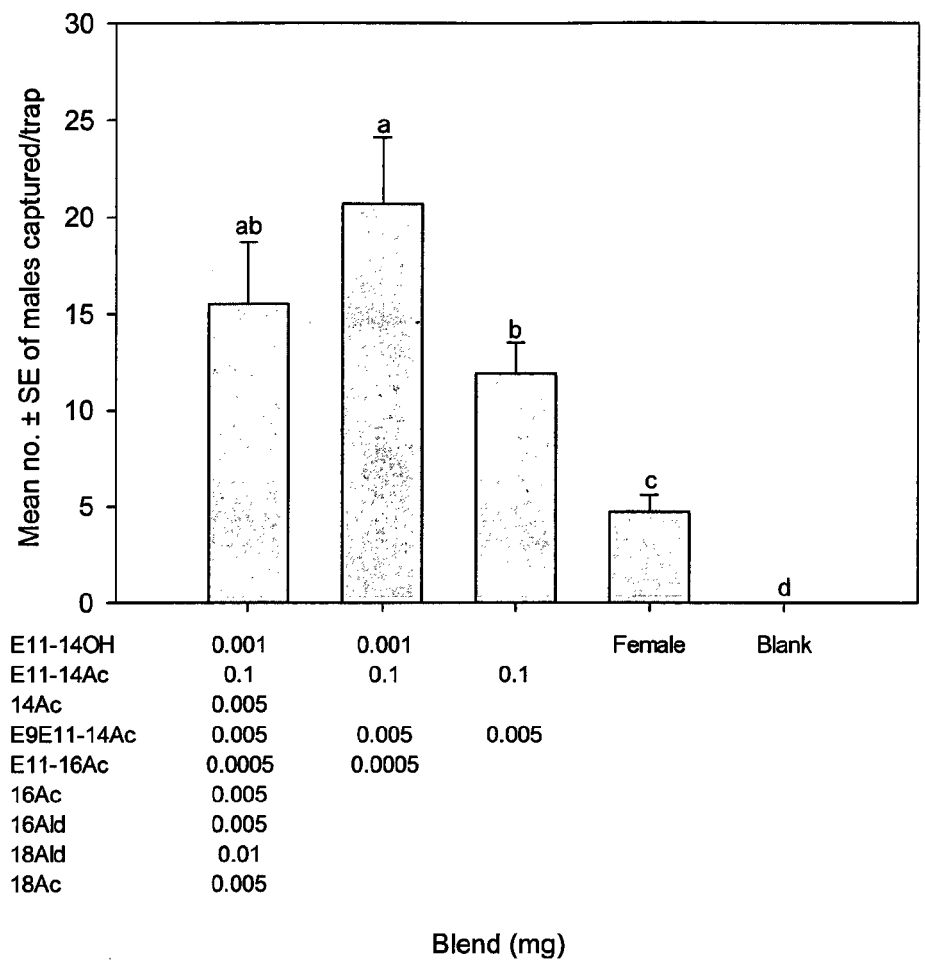

When all compounds identified in the sex pheromone gland were combined in a full blend, the catch was similar to the two-component blend (FIG. 4). Although we tried to mimic the full pheromone blend based on the quality and the quantity of pheromone compounds in the sex gland, this blend might be unrepresentative because some of these compounds might not be emitted from the sex pheromone gland. Repellency might explain the low catch with this blend compared to the four-component blend. Surprisingly, the catch with caged female was low compared to the two component blend (FIG. 4). Previously, traps baited with three females or rubber septa loaded with 105 µg of two components were not significantly from each other (Suckling and Brockerhoff 1999). Here the catch to the binary blend was superior to single females. This could be due to the quality or calling performance of the females used in this experiment. In addition, caged females would be susceptible to weather conditions. Females caught the lowest number of males, and were significantly less attractive than the two-component blend (see FIG. 4).

A final experiment was conducted to test other combination of components of the sex pheromone glands, focusing on the possible role of saturated aldehyde compounds, which were considered unlikely to be active because of the lack of electrophysiological responses. This included:

- a seven-component blend without the two saturated aldehyde compounds (E11-14OH, E11-14Ac, 14Ac, E9E11-14Ac, E11-16Ac, 16Ac, and 18Ac in ratio of 0.001, 0.1, 0.005, 0.005, 0.0005, 0.005, and 0.005 mg respectively),
- a six-component blend without the three saturated acetate compounds (E11-14OH, E11-14Ac, E9E11-14Ac, E11-16Ac, 16Ald, and 18Ald in ratio of 0.001, 0.1, 0.005, 0.0005, 0.005, and 0.01 mg respectively),
- the new four component blend (E11-14OH, E11-14Ac, E9E11-14Ac, E11-16Ac, in ratio of 0.001, 0.1, 0.005, and 0.0005 mg respectively), and
- a two-component blend (E11-14Ac, E9E11-14Ac, in ratio of 0.1 and 0.005 mg respectively).

A trap baited with a blank lure was used as control. The experimental design and protocol of the above two experiments was identical to the above experiments, except that 14 replicates were used in the first experiment and 10 replicates in the second experiment.

Figure 5:
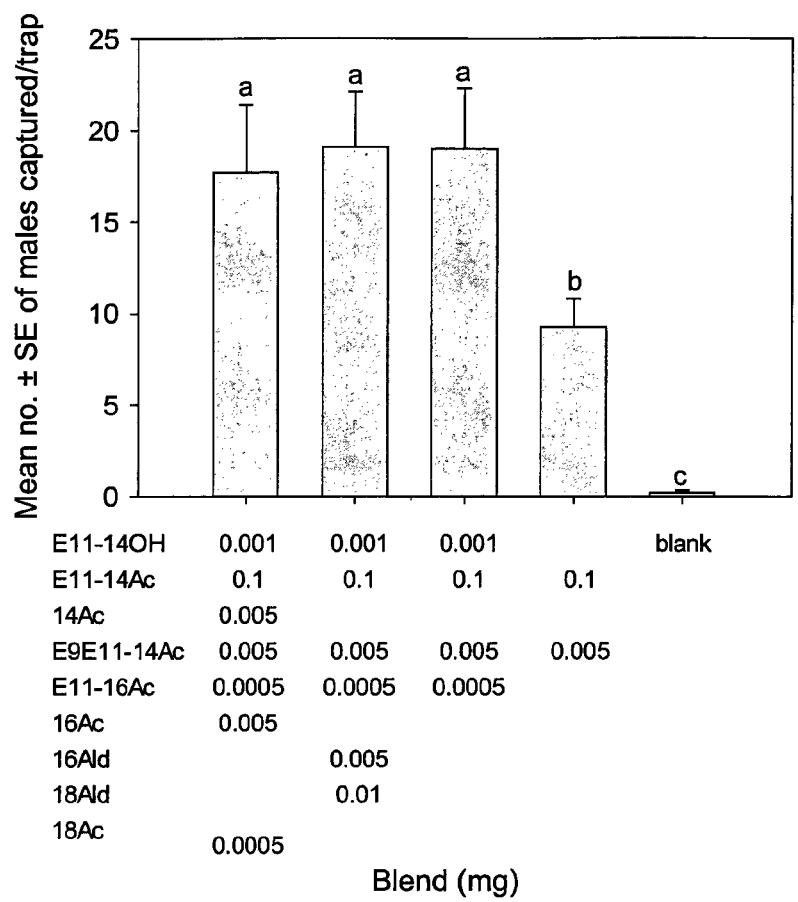

In this experiment, the presence or the absence of saturated aldehyde or acetates didn't have any impact on male catch. All three new blends captured significantly more males than the known two-component blend (FIG. 5). On the other hand, there was no difference in trap catch between the four-component blend, full bend without saturated acetates, or the full blend without saturated aldehydes.

6.2 2011 Experiments

The new four component sex pheromone blend was examined for efficacy of disruption of mating in the laboratory, and in field trials. Large vineyard trials had plot sizes of 30×30 m (Trial 1) and 80×80 m (Trial 2) and examined: a) two component ((E)-11-tetradecenyl acetate and (E,E)-9,11-tetradecadien-1-yl acetate, 95:5), b) four component ((E)-11-tetradecenyl acetate and E,E-9,11-tetradecadien-1-yl acetate plus (E)-11-tetradecen-1-ol and (E)-11-hexadecenyl acetate (10:0.5:0.1:0.05)) blends, c) a higher ratio of the two new minor compounds (10:0.5:10:10), d) with an antagonist ((Z)-11-tetradecenyl acetate) added, and e) without the most expensive pheromone component (E,E-9,11-tetradecadien-1-yl acetate), compared with f) untreated controls.

Results:

In the laboratory, 69.0% of untreated pairs mated, and mating was suppressed by both attractive blends (41.1% mating ($p=0.024$, two component blend), and 18.4% mating ($p=0.003$, four component blend). In vineyards, totals of 24,776 and 41,053 moths were caught in the two trials, respectively, to delta traps baited with four component lures and virgin females. Compared to the two component blend, mating disruption was achieved at a higher level with a four component blend.

Conclusions:

Disruption was on average improved by 12% with the four component blend compared to the two component blend, but this difference was not strongly significant ($p=0.091$). There was evidence to support a role in reducing disruption by the antagonist. Catch to SPLAT indicated much lower attraction than to rubber septa or caged females, suggesting that false trail following was unlikely to be as important as habituation or sensory overload.

The experiments reported here tackle the question of the effect of additional components on behaviour relating to control through mating disruption or lure and kill.

In addition to the comparison of efficacy of two and four component blends as disruptants, there was a rationale and capacity for additional treatments in order to test the possible effect of (Z)-11-tetradecenyl acetate) (Z11-14:Ac) as a disruptant, since this compound was reported as an antagonist for attraction (Rumbo et al., 1993), (Stephens et al., 2008) but its role in mating disruption was unclear. In practice, the lack of separation of the Z11—from the attractive isomer E11-14:Ac in the industrial process (Shin Etsu Fine Chemicals, Tokyo) used for mating disruption of this species means that at 20% of the blend it represents a potentially active impurity in the pheromone, preventing attraction of males to point sources (Rumbo et al., 1993). An estimated 20 tonnes of E-11-14:Ac was stockpiled originally destined for aerial treatment of California against *Epiphyas postvittana* in California (Suckling and Brockerhoff, 2010).

Experimental Methods

Insects

A colony of LBAM was established and maintained at Mt. Albert Research Center (Auckland). The insects were sexed in the pupal stage, and adult males were allowed to emerge in isolation from the females. Males and females were kept at 22±2° C., 18L:6D, they were provided with water and were 2-3 days old at the time of testing. Females were placed in gauze cages inside delta traps placed in the vineyard and checked weekly for male catch and longevity.

Chemicals

All compounds used as authentic standards in the chromatographic analysis or in the field trapping experiments were >97% pure by GC analysis and stored at −80° C. until used. Samples of E11-14:Ac, E9E11-14:Ac, E11-14:OH and E11-16:Ac were purchased from Plant Research International, Wageningen, The Netherlands. All blends of synthetic compounds were applied to the large "well" of red rubber septa (West Pharmaceutical Services, Kearney, N.E., USA) in 200 µl of n-hexane GR (Merck Ltd, New Zealand). The solvent was allowed to evaporate in a fume hood and the septa were stored in heat-sealed foil bags at −20° C. until ready for use. For traps used in assessing disruption, lures contained the four component lure at 1 mg loading with the blends shown in Table 1. Red delta traps with sticky bases (Clare et al., 2000)) were placed on wires at 1 m height and checked weekly. SPLAT LBAM, a wax-based amorphous polymer carrier, was prepared with 10% pheromone and shipped from ISCA Technologies, Riverside, Calif., with Blends 1-5 (Table 2). Samples of E11-14:Ac, E9E11-14:Ac, E11-14:OH and E11-16:Ac were also purchased from ISCA Technologies.

TABLE 2

Constituents of the pheromone blends used in the disruption Trials, along with estimates of the compound present in a female (ng).

| Compound | ng/female in gland[1] | Blend 1 | Blend 2 | Blend 3 | Blend 4 | Blend 5 |
|---|---|---|---|---|---|---|
| E11-14 OH | 0.01 | | 0.1 | 10 | 10 | 10 |
| E11-14 Ac | 9.18 | 10 | 10 | 10 | 10 | 10 |
| E9,E11-14 Ac | 0.48 | 0.5 | 0.5 | 0.5 | 0.5 | — |
| E11-16 Ac | 0.05 | | 0.05 | 10 | 10 | 10 |
| Z11-14 Ac | — | | | | 2.5 | 2.5 |

[1]El-Sayed et al. (2011a)

Laboratory Mating Test

We hypothesized that better disruption would result with the four component blend than with the two component blend, which did not catch as well in traps as a four component blend (El-Sayed et al., 2011a). We were concerned that there might be unrepresentative conditions if assays were set up at a certain time of day, so two light phases were used. Pairs of two-day old moths (1 ♀, 1 ♂) were placed in small cages (680 ml plastic boxes) either with rubber septa loaded with one mg of either a two or a four component blend (Blend 1 and Blend 2 in Table 2), or without a septa. Several runs were done, either using the standard phase (natural day-night cycle), or reverse phase (opposite to natural cycle). The control was used in each run, with just one of the two treatments. Numbers of pairs per run per treatment varied from 9 to 19, but was generally 15. After 24 hours, the female moth in each container was dissected to determine whether it was mated. The number of mated females out of the total pairs was recorded.

Vineyard Trials

An insecticide-free vineyard at Dunstaffnage, Waipara, North Canterbury New Zealand (43.05° S, 172.76° E) was used to conduct three trials. First, (Small Vineyard Trial) in order to understand possible mechanisms of disruption involving attraction, we conducted a trapping test of the attractiveness of dollops of SPLAT containing the two and four component blends (Blends 1 and 2) or blend variations (Blends 3-5), Table 2), single virgin females and a rubber septa loaded at 1 mg with Blend 2. Traps were set at 15 m spaces with ten replicates of the seven treatments, laid out in a randomised block layout modified to fit the property. The number of male moths caught in each trap was recorded weekly for two weeks.

Next, we hypothesised that improved disruption would result from provision of the full four component blend, which we tested in two large trials (Large Vineyard Trials 1 &2). We examined other subsidiary questions at the same time, notably a) the potential impact on catch of higher amounts of the two trace level pheromone compounds, in order to ensure that they were not lost from the formulation, b) the effect of adding the antagonist Z11-14:Ac at 4:1 ratio to the E11-14:Ac, and c) effect on disruption of removal of the most expensive compound, the diene (E,E-9,11-14:Ac). Plots were laid out as 0.09 ha (30×30 m plots, Trial 1) and 0.64 ha (80×80 m plots, Trial 2), with five replicates in both trials. Plots for Large Vineyard Trial 2 were in an approximately rectangular layout, but those for Trial 2 were arranged around two edges of Large Vineyard Trial 1 in an irregular pattern. Treatments were applied in a randomised block layout, with blocks comprising non-contiguous plots, with the traps in each block having a similar pre-trial catch. Traps were operated before and after treatment, in order to assess the background population and trap effects.

Traps were maintained weekly as a short central row transect in each case, with 3 traps containing the four component lure. For Large Vineyard Trial 1, the pre-treatment trapping period extended from Mar. 1-Mar. 16, 2011, with the treated period from Mar. 17-May 4, 2011. For Large Vineyard Trial 2, the pre-treatment period was Mar. 1-Apr. 11, 2011, and treated period was Apr. 12-May 3, 2011, the treatments having been put out in week 6. For this trial, four traps with caged 2 day-old single females were added to each plot from the 13th week. Traps with females were collected and replaced weekly until the end of the trial (17th week; 10th week after treatment). For both trials, the number of moths in the traps was recorded each week. In the results, weeks are numbered with respect to the week the treatment was applied, with this being week 0.

Statistical Analysis

Data for all four trials was analysed with a hierarchical generalised linear model approach (HGLM, Lee et al., 2006). This method allows the analysis of count or binmoial (percentage) data where there are both fixed (e.g. treatments) and random effects (replicates, run etc.). The importance of the random effects was assessed with a X2 test of the change in the deviance, as implemented in GenStat's HGRTEST procedure (GenStat Committee 2011). Fixed effects, including specific contrasts between treatments, were similarly assessed, using GenStat's HGFTEST procedure (GenStat Committee 2011). Results (mean counts, percentages) are presented along with approximate 95% confidence intervals, which were obtained on the transformed scale (logit or log) and back-transformed.

For the laboratory test of mating disruption, the number of mated moths in each run out of the total moth pairs was analysed initially with binomial-beta HGLM, with phase and their interaction as fixed effects with a binomial error and logit link, and runs as a random effect with a beta error and a logit link. Since there were no strong differences in runs, these were not included in the final analysis, which thus reduced to a standard binomial generalized linear model (McCullagh and Nelder, 1989).

For the Small Vineyard Trial (comparative attractiveness of blends), the number of moths caught per trap in each of the third and fourth weeks, and the total over these weeks were analysed. The treatments were included as fixed effects with a Poisson error and logarithmic link, with random effects included with a gamma error and a logarithmic link. There was some evidence of spatial patterning in the counts, so adjustments were made for these by including replicate as a random effect. Counts as a percentage of the catch in the Septa treatment were derived from the parameter estimates calculated as part of the HGLM fitting process.

For both Large Vineyard Trials 1 and 2, counts for each date were analysed. In addition, the total pre-treatment and post-treatment counts were analysed. As for the Small Vineyard Trial, a Poisson-gamma HGLM was used. Random effects assessed were blocks (replicates), plots within blocks, and spatial position (rows and column as in the Trial plans). In addition to the treatments, for the post-treatment counts, a co-variate for the trap counts in the last pre-treatment week was assessed as a fixed effect. For Large Vineyard Trial 1, random effects were largely limited to plots being more variable than traps within a plot, with no strong spatial effect associated with the replicates. The week 0 trap counts which were included as a covariate for the post-treatment trap counts was largely un-important. Thus, in the final analyses, adjustments were only made for plots. There were stronger spatial trends within Large Vineyard Trial 2, with patterns at most dates relating to the replicates or spatial position. As for Large Vineyard Trial 1, the strongest patterns were associated with the plots, with plots more variable than traps within a plot. The Week 0 trap count covariate included for post-treatment data was found to be important so in the final analyses, additional adjustments were made for these counts for post-treatment data. The analysis approach for female-baited traps was the same, except that there were no pre-treatment counts in female traps to use as a co-variate. Plots were more variable than female-baited traps within a plot (P<0.001), so in the final analyses, adjustments were made for plots.

In the results, predicted mean trap catches are presented. These are adjusted to a mean value of any of the co-variates included in the model, and adjusted to be counts/day. Percentage mating disruption is also presented, also with 95% confidence limits. The percentage mating disruption was calculated directly from the estimates of the treatment effects.

All analyses were carried out with GenStat (GenStat Committee, 2011).

Results

Example 4

Laboratory Mating Test

Mating in laboratory cages (Table 3) varied significantly between the treatments (P=0.006). The percentage of mated females was significantly lower for the 2 and 4 component blends than for the untreated control (P=0.024 and P=0.003 respectively), with less mating for the 4 component blend than for the 2 component blend, though this difference was not significant (P=0.134). The percentage of mated females only varied weakly with phase (P=0.096 for the overall test and P=0.274 for the treatment by phase interaction). A slightly higher percentage of females mated in the reverse than the standard phase (58% c.f. 39%).

TABLE 3

Percentage *Epiphyas postvittana* females mated (95% confidence limits) in laboratory mating tests, for pairs in the presence of rubber septa controls or septa loaded with either two component (Blend 1) or four component (Blend 2) sex pheromone, tested for 24 h under two light phases.

| Treatment | Standard Phase | Reverse Phase | Over All |
|---|---|---|---|
| Control | 66.7 (43.6, 83.8) | 70.7 (50.3, 85.2) | 69.0 (53.9, 80.8) |
| 2-component | 20.0 (6.0, 49.6) | 60.7 (32.6, 83.2) | 41.1 (22.3, 62.9) |
| 4-component | 13.3 (1.5, 60.1) | 23.3 (7.7, 52.7) | 18.4 (6.2, 43.7) |
| Over All | 38.9 (22.4, 58.3) | 57.5 (42.3, 71.4) | |

Example 5

Small Vineyard Trial

The attractiveness of SPLAT dollops measured through relative catch of male *Epiphyas postvittana*, compared to rubber septa or a virgin female moths (total 761 insects caught) is shown in Table 4. At both collection dates, and also therefore for the total count, there were substantial differences between the treatments (P<0.001). Catches with the 4 component lure (Septa Blend 2) were much greater than those for other treatments (P<0.001 at each date and overall), with counts for the other treatments being less than 20% of the lure catch. Catches for the caged females were also greater than for other treatments (P<0.001, P=0.004, P<0.001 at each date and overall), with more than 1.5× as many caught than in the other treatments. However, numbers also varied somewhat between the other treatments (P=0.022, P=0.103, P=0.007 at each date and overall): most notably, catches with the extra minor components above the levels in the female moth gland (Blend 3) were greater than for the other blends.

TABLE 4

Total catch of *Epiphyas postvittana* over 14 days (10 replicates, 95% confidence limits), to 1 g dollops of SPLAT with five blends or positive controls and counts as a percentage of the catch in the lure trap.

| Treatment | 14 day count | % of lure count |
|---|---|---|
| Blend 1 | 17 (6.0, 47.8) | 2.9 (1.1, 7.4) |
| Blend 2 | 24 (9.7, 59.6) | 4.1 (1.9, 9.0) |
| Blend 3 | 40 (18.6, 86.2) | 6.8 (3.7, 12.7) |
| Blend 4 | 18 (6.5, 49.6) | 3.1 (1.2, 7.6) |
| Blend 5 | 1 (0.0, 37.5) | 0.2 (0.0, 6.2) |
| Septa (Blend 2) | 585 (353.3, 968.8) | — |
| Caged female | 76 (39.8, 145.2) | 13.0 (8.2, 20.6) |

Example 6

Large Vineyard Trial 1

A total of 24,776 moths was caught in Large Vineyard Trial 1. Pre-treatment, there were (as anticipated), no significant differences between the treatments (P=0.583 comparing the control with the mean of the treatments, and P=0.875 comparing between treatments). Post-treatment, there was evidence of suppression of catch in all blends over 14 weeks post-treatment (P<0.001 comparing the control with the mean of the treatments). Totaled over all weeks, disruption was reasonably similar for all five blends (P=0.089 comparing between treatments), with Blend 4 (71.7%, with diene) having a slightly weaker disruptive effect than the new four component blend (Blend 2, 89%) or the four component minus diene (Blend 5, 89%). The latter result appears to be anomalous. In 13 of the 14 post-treatment weeks (FIG. 1), disruption was greater with the four component blend (Blend 2) than with the two component blend (Blend 1), with a median difference between the two blends of 4.3 (differences ranging from −0.7 to 24%). Summarized over the post-treatment weeks, disruption was on average 12% less for Blend 1 than Blend 2, but this difference was not strongly significant (p=0.091)

TABLE 5

Estimated mean *Epiphyas postvittana* moth count per trap per day in Large Vineyard Trial 1, and percentage mating disruption (approx. 95% confidence limits)

| | Pre-Treatment | | Post-Treatment | |
|---|---|---|---|---|
| | Count/Trap/Day | % Disruption | Count/Trap/Day | % Disruption |
| Blend 1 | 3.4 (2.2, 5.2) | −36.0 (−156.3, 27.8) | 1.8 (1.0, 3.2) | 77.0 (50.6, 89.3) |
| Blend 2 | 2.7 (1.7, 4.3) | −9.5 (−109.5, 42.8) | 0.8 (0.4, 1.7) | 89.0 (73.8, 95.4) |
| Blend 3 | 2.6 (1.7, 4.2) | −5.8 (−102.9, 44.9) | 1.5 (0.8, 2.7) | 81.0 (58.4, 91.4) |
| Blend 4 | 2.5 (1.6, 4.0) | −0.6 (−93.9, 47.8) | 2.2 (1.2, 3.9) | 71.7 (40.3, 86.5) |
| Blend 5 | 2.8 (1.8, 4.4) | −14.0 (−117.4, 40.2) | 0.8 (0.4, 1.7) | 89.1 (74.0, 95.5) |
| Control | 2.5 (1.6, 4.0) | | 7.7 (4.8, 12.5) | |

Example 7

Large Vineyard Trial 2

A total of 41,053 moths was caught in Large Vineyard Trial 2. This trial, which was larger in area, essentially emulated Large Vineyard Trial 1 and there was reasonable agreement in both tests for the relative and absolute efficacy of all treatments, with the exception of Blend 5. There was noticeably less efficacy for this blend than in Large Vineyard Trial 1. The best disruption results were from the natural blend four component blend (Blend 2, Tables 5 and 6).

As expected pre-treatment, there were no significant differences between the treatments (P=0.908 comparing the control with the mean of the treatments, and P=0.887 comparing between treatments). Post-treatment, disruption was significant for all treatments (P<0.001 comparing the control with the mean of the treatments). Unlike in Large Vineyard Trial 1, disruption varied between the five blends (P<0.001 comparing between treatments), with Blend 4 having a weaker disruptive effect than Blend 1 or Blend 2, and a slightly weaker effect than Blend 3.

Figure 6:
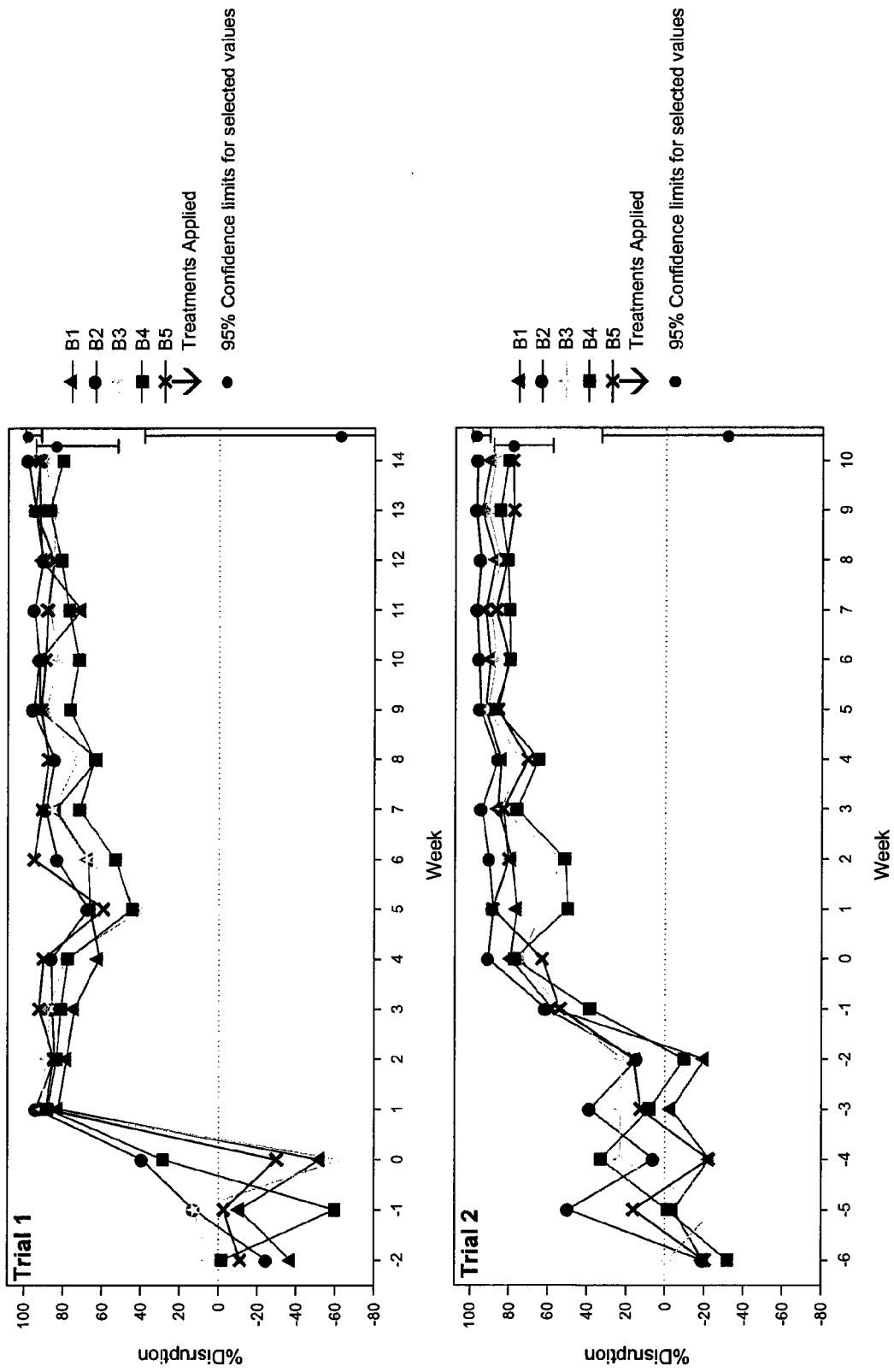
FIG. 6 shows the percentage disruption of *Epiphyas postvittana* catch to four component lures, in comparison to the untreated control for five blends shown in Table 2, for Large Vineyard Trials 1 and 2. Error bars show 95% confidence limits for (typical) indicated means.

Disruption for Blend 2 was greater than that for Blend 3 (p<0.001) indicating that the increase in amounts of the minor components may reduce disruption. Disruption for blend 4 was not as great as for Blend 3 (although not significantly less, p=0.141), indicating that the presence of Z11 has weakened the disruptive effect. Disruption was greater in the four component blend (Blend 2) compared to with the 2 component blend (Blend 1) for all 10 post-treatment weeks (FIG. 6, differences of 1.5 to 12.3% more, median 4.3). This was consequently true for total post-treatment counts, where disruption was 5.3% greater for Blend 2 (but not significantly so, p=0.059).

Figure 7:
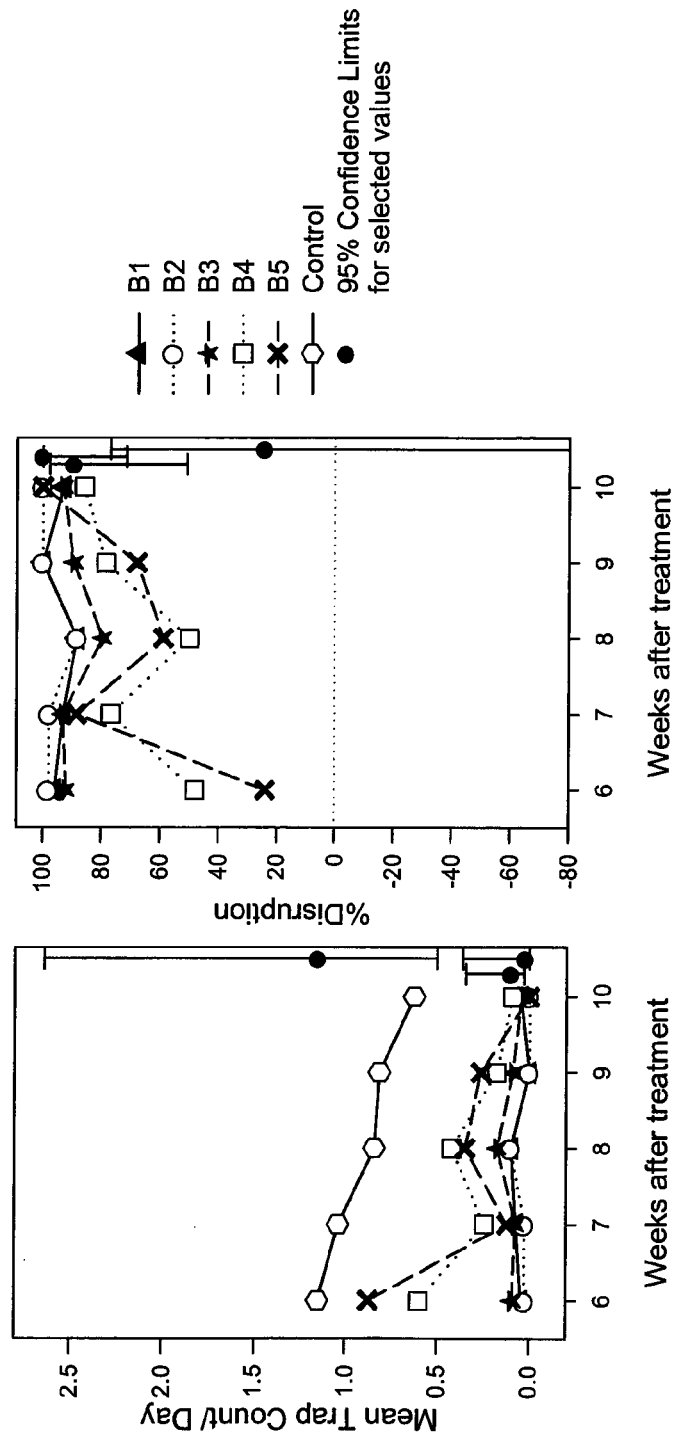
FIG. 7 shows the mean trap count per day of male *Epiphyas postvittana* in female-baited traps and percentage disruption for five blends (Table 2) and an untreated control, for 6-10 weeks after treatment in Large Vineyard Trial 2. Error bars show 95% confidence limits for (typical) indicated means.

With female-baited traps which were operated for five weeks, catches per trap per day were low, and decreased over time with the controls. Counts for treatments Blend 1, Blend 2 and Blend 3 were very low post-treatment. Counts for Blend 4 and Blend 5, although higher, were consistently below those for the controls (FIG. 7). The frequency of occasions with any male catch to female moths was lowest to Blend 2 (2 of 40 trapping occasions), followed by Blend 1 (4), Blend 3 (6), Blend 4 (12), Blend 5 (14) and highest in the untreated control (24).

Disruption was substantial for all treatments (P<0.001 comparing the control with the mean of the treatments, Table FIG. 7), with disruption varying between the five blends (P<0.001). Blends 4 & 5 had a weaker disruptive effect than Blend 1 or Blend 2, and a slightly weaker effect than Blend 3.

Discussion

The four component blend (1 mg loading) was more attractive to male moths than female moths (FIG. 6), indicating that the assessment of disruption of these lures was likely to be conservative, by underestimating efficacy of disruption of females, thus understating suppression that might be achieved in comparison with the field population. This was corroborated by comparison of disruption levels to lures or females (which were more disrupted). The results are based on relatively large samples of insects, and it has been possible to see effects from changing the ratio of minor compounds or adding the inhibitor.

Better disruption resulted from the natural four component blend, and the commercial blend with Z11-14:Ac was less disruptive to males than the natural blend. Therefore, the behavioral inhibitor Z11-14:Ac acts as an antagonist to attraction and is also antagonistic to disruption.

Better disruption is the target but current industrial supplies have significant amounts (~20%) of inhibitor present which appears from our results to reduce efficacy when it is present. Reliance on expensive pheromone of high purity may not be a significant issue since more pheromone plus inhibitor can also be successfully used (Suckling and Brockeroff 2010), although more of this cheaper mix would be needed.

TABLE 6

Estimated mean *Epiphyas postvittana* moth count per trap per day in Large Vineyard Trial 2, and percentage mating disruption (approx. 95% confidence limits)

| | Pre-Treatment | | Post-Treatment | |
|---|---|---|---|---|
| | Count/Trap/Day | % Disruption | Count/Trap/Day | % Disruption |
| Blend 1 | 1.7 (1.2, 2.5) | 8.1 (−26.5, 33.2) | 1.2 (0.8, 1.9) | 87.0 (79.9, 91.6) |
| Blend 2 | 1.7 (1.2, 2.5) | 8.4 (−26.4, 33.7) | 0.7 (0.4, 1.2) | 92.3 (87.2, 95.3) |
| Blend 3 | 1.9 (1.3, 2.7) | −0.7 (−38.5, 26.8) | 1.8 (1.2, 2.7) | 81.2 (71.6, 87.6) |
| Blend 4 | 1.9 (1.4, 2.7) | −2.5 (−40.2, 25.0) | 2.4 (1.6, 3.6) | 74.1 (61.9, 82.5) |
| Blend 5 | 1.9 (1.4, 2.8) | −2.8 (−41.0, 25.0) | 2.0 (1.3, 2.9) | 78.9 (68.4, 85.9) |
| Control | 1.9 (1.3, 2.7) | | 9.3 (6.6, 13.2) | |

The smaller trial had some evidence of confounding between Blend 2 and two downwind plots with Blend 5, which probably explains the anomalously high disruption in Large Vineyard Trial 1.

Mobile mating disruption (Suckling et al. 2011) could not address the role of Z11-14:Ac in disruption because of difficulties in achieving the same payload in the high and low purity E11-14:Ac treatments for the amount of active pheromone present, but experiments here are clear that addition of Z11-14Ac reduced disruption, as it does for attraction (Rumbo et al. 1983).

The durability of the pheromone treatment with SPLAT was more than 14 weeks under the prevailing temperatures.

7. INDUSTRIAL APPLICABILITY

The four component pheromone compositions of the invention have been found to be twice as efficacious as the standard two component blend currently used. Therefore the pheromone compositions have application as attractants for male LBAM. As such, they can be used to control or monitor LBAM populations by a variety of methods including attracting the male moths to traps and disruption of mating.

The enhanced activity means that the new more attractive blend may be used in areas of low population density such as newly invaded habitats where the standard two component blend might not be sufficiently attractive. The enhanced efficacy of the new pheromone blend also means that a smaller amount can be used to attract the LBAM, resulting in cost savings.

REFERENCES

Bellas, T. E.; Bartell, R. J.; Hill, A., 1983. Identification of two components of the sex pheromone of the moth, *Epiphyas postuittana* (Lepidoptera:Torticidae). *J. Chem. Ecol.* 9:50-512.

El-Sayed, A. M., Suckling, D. M., Wearing, C. H. and Byers, J. A. 2006. Potential of mass trapping for long-term pest management and eradication of invasive species. *J. Econ. Entomol.* 99:1550-1564.

El-Sayed, A. M., Suckling, D. M., Byers, J. A, Jang E. B., and Wearing, C.H.2009. Potential of "lure and kill" for long-term pest management and eradication of invasive species. *J. Econ. Entomol.* 102: 815-835.

El-sayed, A. M. 2010. The Pherobase: Database of Insect Pheromones and Semiochemicals. http://www.pherobase.com Foster, S. P., Roelofs, W. L. 1990. Biosynthesis of a monoene and a conjugated diene sex pheromone component of the light brown apple moth by D11 desaturation. *Experientia* 46:269.273.

Gray, T. G., Slessor, K. N., Grant, G. G., Shepherd, R. F., Holsten, E. H., and Tracey, A. S. 1984. Identification and field testing of pheromone components of *Choristoneura orae* (Lepidoptera: Torticidae). *Can. Entomol.* 116:51-56.

Muggleston, S. J. and S. P. Foster 1989. Sustained-Flight Tunnel Responses of Male Light-Brown Apple Moth to Synthetic Sex-Pheromone. *Physiological Entomology* 14(4): 443-449.

Neal, J. W., Jr., Klun, J. A., Bierl-Leonhardt, B. A., and Schwarz, M. 1982. Female sex pheromone of *Choristoneura parallela* (Lepidoptera: Torticidae). *Environ. Entomol.* 11:893-896.

Sas Institute Inc. 1998. Statview. Cary, N.C.: SAS Institute Inc.

Suckling, D. M. and Brockerhoff, E.G. 2010. Invasion biology, ecology, and management of the light brown apple moth (Tortricidae). *Ann. Rev. Entomol.* 55: 285-306.

Suckling, D. M., and Shaw, P. W. 1992. Conditions that favor mating disruption of *Epiphyas postvittana* (Lepidoptera: Tortricidae). *Env. Ent.* 21: 949-956.

Suckling, D. M. and E. G. Brockerhoff. 1999. Control of light brown apple moth, *Epiphyas postvittana* (Lepidoptera: Tortricidae) using an attracticide. *J. Econ. Entomol.* 92: 367-372.

CLARE, G., SUCKLING, D. M., BRADLEY, S. J., WALKER, J. T. S., SHAW, P. W., DALY, J. M., MCLAREN, G. F., and WEARING, C. H. 2000. Pheromone trap colour determines catch of non-target insects. New Zealand Plant Protection 53:216-220.

DUMBLETON, L. J. 1935. Apanteles tasmanica Cam.: A Braconid parasite of leafroller larvae. New Zealand Journal of Science and Technology 17:572-576.

EL-SAYED, A., MITCHELL, V., MANNING, L.-A., and SUCKLING, D. 2011a. New Sex Pheromone Blend for the Lightbrown Apple Moth, *Epiphyas postvittana*. Journal of Chemical Ecology 37:640-646. DOI 10.1007/s10886-011-9964-x.

EL-SAYED, A. M., MITCHELL, V. J., MANNING, L.-A. M., and SUCKLING, D. M. 2010. New Sex Pheromone Blend for the Lightbrown Apple Moth, *Epiphyas postvittana*. Patent No.

EL-SAYED, A. M., MITCHELL, V. J., MANNING, L.-A. M., and SUCKLING, D. M. 2011b. New Sex Pheromone Blend for the Lightbrown Apple Moth, *Epiphyas postvittana*. Journal of Chemical Ecology 37:640-646. DOI 10.1007/s10886-011-9964-x.

GENSTAT COMMITTEE. 2011. The Guide to GenStat Release 14—Parts 1-3. R. W. Payne, (ed.). VSN International, Oxford.

MCCULLAGH, P. and NELDER, J. A. 1989. Generalized Linear Models. 2nd edn. Chapman & Hall, London.

MINKS, A. K. and CARDE, R. T. 1988. Disruption of Pheromone Communication in Moths—Is the Natural Blend Really Most Efficacious. Entomologia Experimentalis et Applicata 49:25-36.

RUMBO, E. R., DEACON, S. M., and REGAN, L. P. 1993. Spatial discrimination between sources of pheromone and an inhibitor by the light-brown apple moth *Epiphyas postvittana* (Walker) (Lepidoptera: Tortricidae). Journal of Chemical Ecology 19:953-962.

STEPHENS, A. E. A., SUCKLING, D. M., and EL-SAYED, A. M. 2008. Odour quality discrimination for behavioural antagonist compounds in three tortricid species. Entomologia Experimentalis et Applicata 127:176-183. DOI http://dx.doi.org/10.1111/j.1570-7458.2008.00694.x.

SUCKLING D. M., G. F., M., L. M., M., . . . , M. V. J., B., A., K., C., and M., E.-S. A. 2011. Development of single dispensers for suppression of *Epiphyas postvittana, Planotortrix octo, Ctenoseustis obliquana* in New Zealand Stonefruit orchards. Pest Management Science in press.

The invention claimed is:
1. A pheromone composition comprising:
  (a) E11-14Ac;
  (b) E9E11-14Ac;
  (c) E11-14OH; and
  (d) E11-16Ac;
wherein (a) and (b) are present in a weight ratio of about 50:5 to about 150:5, and (c) and (d) are present in a ratio of about 5:1 to about 1:2 that increases effectiveness of the composi- tion at attracting male light brown apple moths (LBAM) relative to a pheromone composition comprising (a) and (b) only.

2. The pheromone composition of claim 1 wherein (a) and (c) are present in a ratio of about 300:1 to about 20:1.

3. A pheromone composition, comprising:
   (a) E11-14Ac at a concentration of about 250 to about 750 µg/ml;
   (b) E9E11-14Ac at a concentration of about 10 to about 40 µg/ml;
   (c) E11-14OH at a concentration of about 2 to about 8 µg/ml;
   (d) E11-16Ac at a concentration of about 1 to about 4 µg/ml; and
   (e) a liquid carrier.

4. The pheromone composition of claim 3 wherein the liquid carrier is an organic solvent comprising one or more of pentane, hexane, and heptane.

5. A method of attracting male light brown apple moths (LBAM) to a location, comprising providing an effective amount of the pheromone composition of claim 1 to the location.

6. The method of claim 5 wherein the male LBAM are subsequently or simultaneously exposed to a killing agent that kills the moths.

7. The method of claim 5 wherein the location comprises either (i) one or more traps, or (ii) one or more traps that contain a killing agent.

8. The method of claim 6 wherein the killing agent is an insecticide.

9. A method of disrupting mating of light brown apple moths (LBAM) comprising providing to a population of LBAM an effective amount of the pheromone composition of claim 1.

10. The pheromone composition of claim 1 which comprises (a) E11-14Ac in a weight ratio of about 50 to about 150; (b) E9E11-14Ac in a weight ratio of about 5; (c) E11-14OH in a weight ratio of about 0.2 to about 1; and (d) E11-16Ac in a weight ratio of about 0.1 to about 2.

11. The pheromone composition of claim 1 which comprises (a) E11-14Ac in a weight ratio of about 100; (b) E9E11-14Ac in a weight ratio of about 5; (c) E11-14OH in a weight ratio of about 1; and (d) E11-16Ac in a weight ratio of about 0.5.

12. The pheromone composition of claim 1 which comprises (a) E11-14Ac in a weight ratio of about 50 to about 150; (b) E9E11-14Ac in a weight ratio of about 2 to about 10; (c) E11-14OH in a weight ratio of about 1; and (d) E11-16Ac in a weight ratio of about 0.1 to about 2.

13. The pheromone composition of claim 3 wherein the concentration of (a) is about 500 µg/ml, wherein the concentration of (b) is about 25 µg/ml, wherein the concentration of (c) is about 5 µg/ml, and wherein the concentration of (d) is about 2.5 µg/ml.

* * * * *